US005610796A

United States Patent [19]

Lavene

[11] Patent Number: 5,610,796
[45] Date of Patent: *Mar. 11, 1997

[54] METALLIZED CAPACITOR HAVING INCREASED DIELECTRIC BREAKDOWN VOLTAGE AND METHOD FOR MAKING THE SAME

[75] Inventor: Bernard Lavene, Ocean, N.J.

[73] Assignee: Electronic Concepts, Inc., Eatontown, N.J.

[ * ] Notice: The term of this patent shall not extend beyond the expiration date of Pat. No. 5,608,600.

[21] Appl. No.: 198,846

[22] Filed: Feb. 18, 1994

Related U.S. Application Data

[63] Continuation-in-part of Ser. No. 20,344, Feb. 19, 1993, and Ser. No. 127,867, Sep. 28, 1993.

[51] Int. Cl.⁶ .............. H01G 4/005; H01G 4/32; H01G 7/00
[52] U.S. Cl. .............. 361/303; 361/301.5; 361/273; 29/25.42
[58] Field of Search .............. 361/301.5, 303, 361/304, 305, 309, 323, 273; 29/25.42

[56] References Cited

U.S. PATENT DOCUMENTS

| | | | |
|---|---|---|---|
| 3,185,907 | 5/1965 | McKee et al. | |
| 3,457,478 | 7/1969 | Lehrer. | |
| 3,585,468 | 6/1971 | Chertok et al. | 361/301.5 |
| 3,602,770 | 8/1971 | McMahon | 361/11 |
| 3,628,108 | 12/1971 | Craig et al. | 361/304 |
| 4,072,976 | 2/1978 | Harari | 361/273 |
| 4,306,274 | 12/1981 | Yamagiwa et al. | 361/304 |
| 4,320,437 | 3/1982 | Shaw et al. | 361/303 |
| 4,470,097 | 9/1984 | Lavene | 361/304 |
| 4,516,187 | 5/1985 | Lavene | 361/309 |
| 4,642,731 | 2/1987 | Shedigian | 361/319 |
| 4,685,026 | 8/1987 | Lavene | 29/25.42 |
| 4,719,539 | 1/1988 | Lavene | 361/307 |
| 4,926,862 | 5/1990 | Miyajima et al. | 428/419 |
| 5,019,418 | 5/1991 | Linzey et al. | 29/25.42 |

FOREIGN PATENT DOCUMENTS

| | | | |
|---|---|---|---|
| 607826 | 11/1960 | Canada | 361/323 |
| 44710 | 2/1990 | Japan. | |
| 2-44710 | 2/1990 | Japan | 361/273 |
| 4311017 | 11/1992 | Japan | 361/273 |
| 1138409 | 1/1969 | United Kingdom | 361/273 |

*Primary Examiner*—Bot L. Ledynh
*Attorney, Agent, or Firm*—Ratner & Prestia

[57] ABSTRACT

A metallized film capacitor in which the metallization is made as thin as possible in order to increase the dielectric strength of the film. In the industry, typical metallization thicknesses range from approximately 1–4 ohms/sq, however, the present invention employs thicknesses which range from 5–300 ohms/sq. And, depending on which thickness is used, the effective dielectric strength of the film can be substantially increased.

19 Claims, 5 Drawing Sheets

METALLIZED CAPACITOR HAVING INCREASED DIELECTRIC BREAKDOWN VOLTAGE AND METHOD FOR MAKING THE SAME This application is a continuation-in-part application of pending parents U.S. patent application Ser. No. 08/020,344, filed Feb. 19, 1993, and U.S. patent application Ser. No. 08/127,867, filed Sep. 28, 1993.

FIELD OF THE INVENTION

The invention relates generally to a metallized film capacitor and more particularly to varying the metallization of a metallized film capacitor.

BACKGROUND OF THE INVENTION

A standard metallized film capacitor widely known in the art is the wound capacitor. Wound capacitors are constructed by sandwiching a dielectric film such as polycarbonate, polypropylene or polyester film between metal electrodes (e.g., vapor deposited metal film). Once formed, the combination dielectric/metal material is wound to form a capacitor. Some specific examples of wound capacitors are found in the following: U.S. Pat. No. 4,320,437 (Shaw et al.), U.S. Pat. No. 4,719,539 (Lavene), and U.S. Pat. No. 4,685,026 (Lavene).

The maximum electrostatic energy that can be stored in a metallized film capacitor depends on the total capacitance of the capacitor and the square of the maximum voltage that can be safely applied across the capacitor (its breakdown voltage). The breakdown voltage of a capacitor depends on the dielectric strength and the thickness of the film.

Related to the breakdown voltage is the number of shots a capacitor, when used as an energy storage device, can withstand. A "shot" is the two step process of (1) charging the capacitor and, then, (2) discharging the stored energy, in the form of a pulse, into a low impedance load (e.g., (1) a human body is approximately a 40 ohm load and (2) a strobe is approximately a 4 ohm load). For general applications, capacitors are rated such that they can withstand on the order of 100,000 shots; however, special applications may only require a limited number of shots.

Also related to the breakdown voltage is the size of the capacitor. The size of a metallized film capacitor is substantially dictated by the thickness of its dielectric film. The thickness of the dielectric, in turn, is dictated by the required overall breakdown voltage of the capacitor. For instance, if a manufacturer cites a particular film as having a dielectric strength of 200 volts/$\mu$ and the capacitor design calls for a dielectric breakdown voltage of 400 volts, then the film may be 2$\mu$ thick.

It should be noted that the thickness of the metallization (typically referred to in ohms/sq), although it contributes to the size, is not as substantial as that of the dielectric. Typical metallization thickness range from approximately 1–4 ohms/sq.

Electrolytic capacitors have been commonly used as energy storage devices because they can be made small with high energy storage capability. However, electrolytic capacitors have many drawbacks. The drawbacks include: (1) a high dissipation factor, (2) capacitance decreases with increasing frequency, (3) capacitance substantially decreases with decreasing temperature, (4) because electrolytic capacitors are very lossy, they produce only about 80% efficiency on discharges, (5) electrolytic capacitors tend to leak and (6) if electrolytic capacitors remain idle for an extended period of time, the oxide on the aluminum must be reformed which requires precious battery power.

A particular application for which electrolytic capacitors have been used instead of metallized film capacitors, primarily because of size requirements, is in implantable defibrillators. In a recent IEEE Spectrum article, however, discussing implantable defibrillators, it was stated that "[f]uture generations of defibrillators are likely to be smaller. Today's models are about the size of a bar of soap, and shrinking them further will require new kinds of batteries and capacitors. Defibrillator manufacturers, who currently use aluminum electrolytic photoflash capacitors, are working on custom capacitors that will help reduce implant size." *IEEE Spectrum*, "Technology 1993", January 1993, pg. 76, col. 3.

In an implantable defibrillator, the capacitor is used as an energy storage device. A battery is used to charge the capacitor which, in turn, delivers a shot to the patient's heart in order to correct, for instance, ventricular tachycardia (ventricles beating to rapidly) or ventricular fibrillation (ventricle quiver chaotically). In an implantable defibrillator, the capacitor need only be capable of delivering from 3 to 6 shots. Practically speaking, if the defibrillator is unable to correct the problem within 6 shots, it is unlikely that the patient will survive, hence, eliminating the need for additional shots.

Thus, it would be advantageous, particularly for applications such as implantable defibrillators, to have metallized film capacitors which match, or even better, the size of comparable electrolytic capacitors.

SUMMARY OF THE INVENTION

The present invention involves varying the thickness of the metallization on a metallized film capacitor in order to effectively vary the dielectric strength of the dielectric film which, consequently, varies the dielectric breakdown voltage of the capacitor.

BRIEF DESCRIPTION OF THE DRAWINGS

The invention is best understood from the following detailed description when read in connection with the accompanying drawings, in which.

DETAILED DESCRIPTION OF THE INVENTION

The present invention involves varying the metallization thickness on a metallized film capacitor in order to effectively vary the dielectric strength of the dielectric film.

Figure 1:
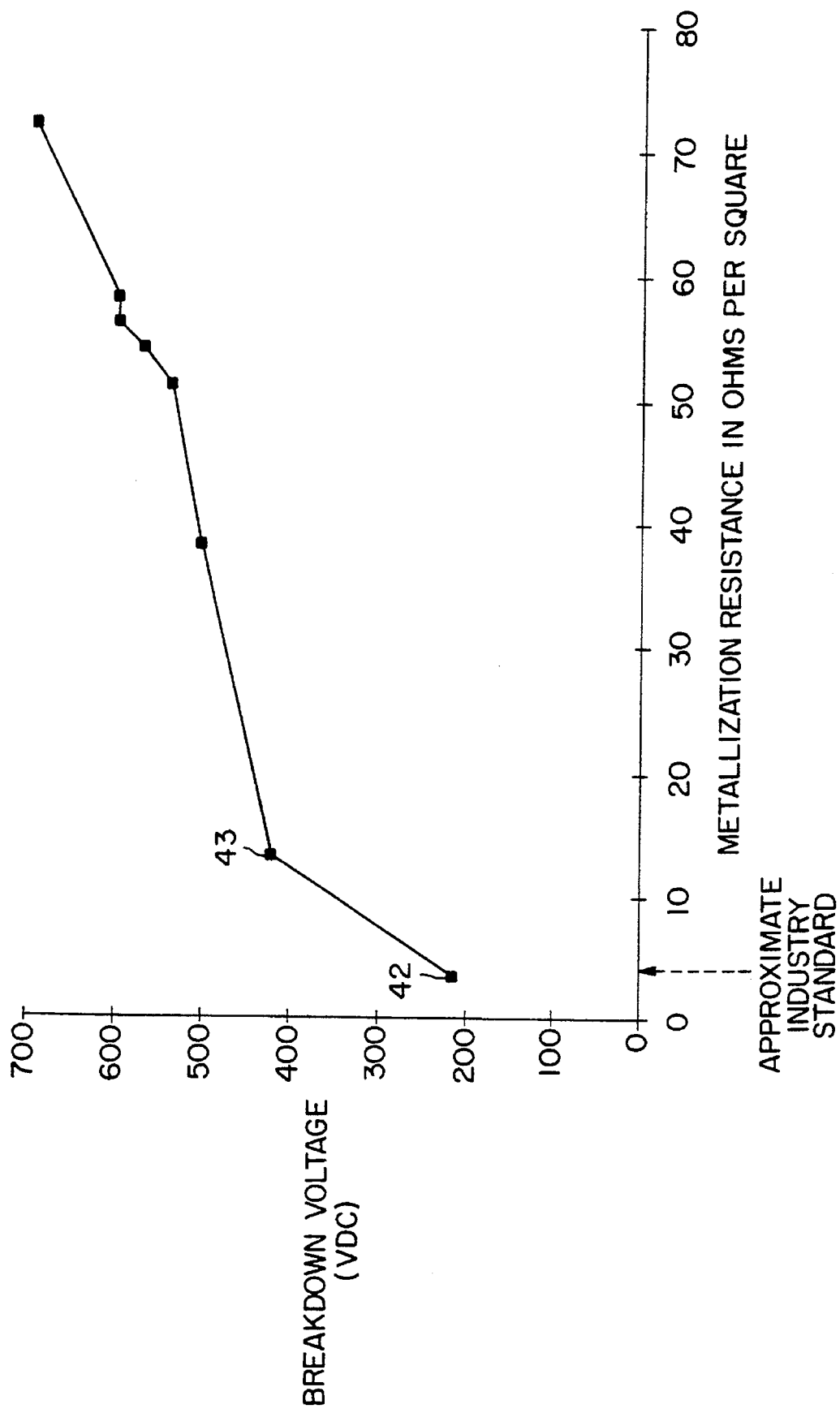
FIG. 1 is a graph illustrating the relationship between metallization thickness and dielectric breakdown voltage.

FIG. 1 is a graph illustrating the relationship between metallization thickness and dielectric breakdown voltage. The graph shows, for example, that increasing the metallization resistance by 3–4 times (from 4 ohms/sq at point 42 to 14 ohms/sq at point 43) the breakdown voltage is increased by approximately 2 times (from 210 volts/μ to 420 volts/μ). It should be noted that reducing the metallization thickness increases the metallization resistance through differing slopes.

The ability to vary the dielectric strength of a dielectric film without increasing its thickness translates into smaller metallized film capacitors with higher dielectric breakdown voltages. The practical consequence of this is potentially quite broad.

Metallized film capacitors employing the present invention can match, and even better, the small size of electrolytic capacitors. For example, to match the size of a comparable electrolytic capacitor, the dielectric strength of a given film would have to increase from approximately 200 volts/μ to approximately 300 volts/μ. By reducing the metallization thickness in accordance with the present invention, the dielectric strength of the film can be increased from 200 volts/μ to approximately 700 volts/μ.

In the capacitor industry, standard metallization thicknesses vary from 1–4 ohms/sq. The exemplary embodiment of the present invention makes the metallization as thin as possible without losing the capacitor (i.e. there is no metal, hence, no electrode). In addition, the metallization should be as thin as possible while retaining the ability to handle various levels of ripple current, as for example approximately 3%–5%. Currently, metallization thicknesses within the range of 5–300 ohms/sq have been achieved. By varying the metallization thicknesses, the dielectric strengths of some films cited by manufacturers have been effectively increased by as much as 250%.

One example of this is a dielectric known as PEN manufactured by DuPont. DuPont's accompanying product literature indicates that PEN has a dielectric strength of approximately 230 volts/μ. By reducing the thickness of the metallization to between 40–70 ohms/sq, the effective dielectric strength was increased to approximately 530 volts/μ.

The effectively increased dielectric strength allows for the production of smaller capacitors with higher dielectric strengths which are needed, for example, in devices such as implantable defibrillators.

Additionally, it should be noted that ideal dielectric strengths or intrinsic voltage values (determined in laboratory tests using polished electrodes and oil by manufacturers such as DuPont) for polyester films which range from approximately 15,000–20,000 volts/mil are difficult, if not impossible, to achieve this ideal in practice (i.e., in a commercially made capacitor). The dielectric strengths achieved in practice are generally about ¼ of the ideal; however, by making the metallization thickness as thin as possible, dielectric strengths in practice may be made greater than ½ of the ideal or approximately 12,000 volts/mil.

The exemplary embodiment of the present invention uses many of the construction techniques found in U.S. Pat. No. 4,470,097 (Lavene) which is herein incorporated by reference.

Figure 2:
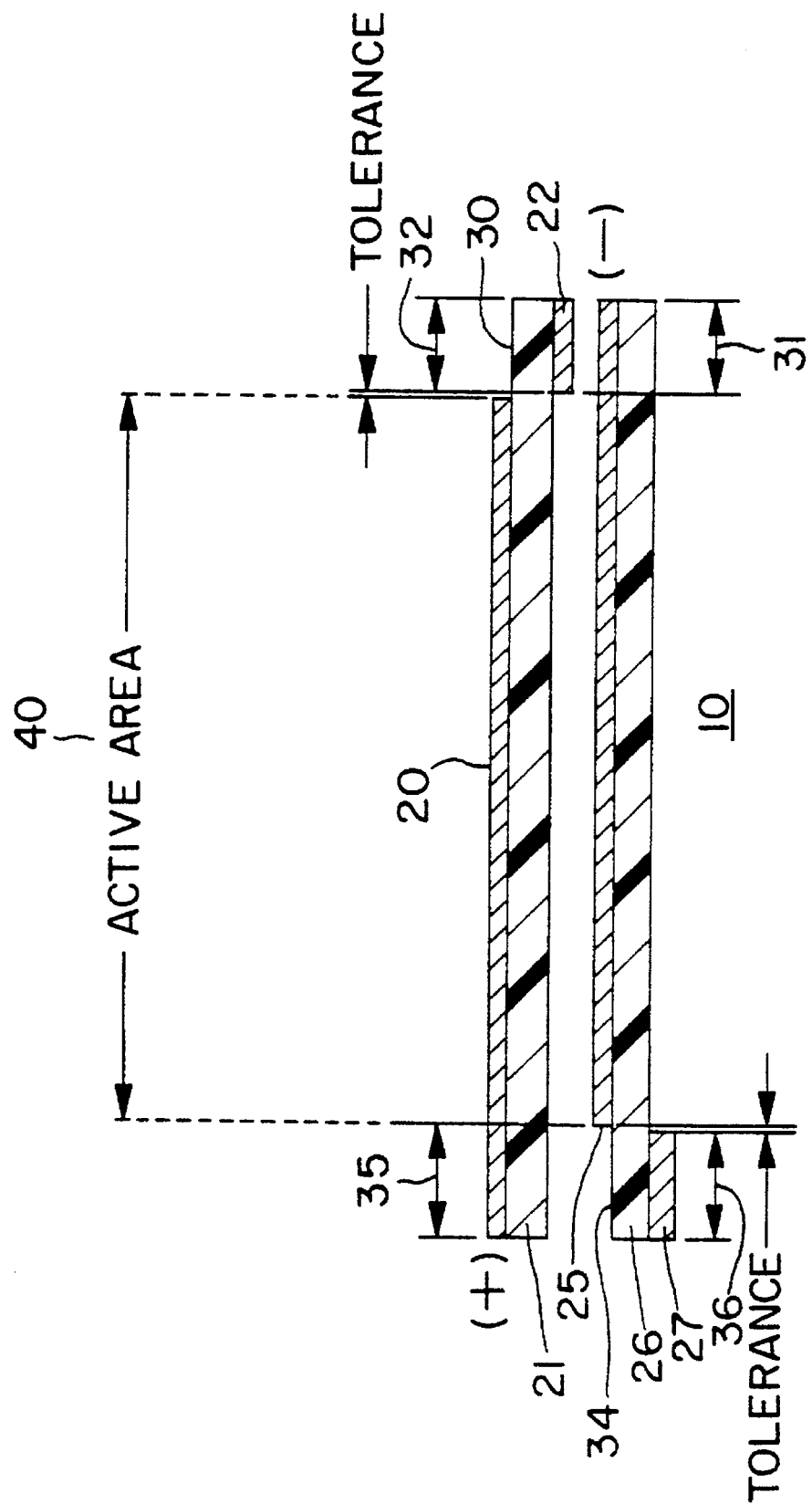
FIG. 2 shows a first exemplary embodiment of a metallized film capacitor employing the present invention.

FIG. 2 shows a wound capacitor 10 comprising a first elongated dielectric web 21 having an electrode 20 metallized on an upper face thereof. A second elongated dielectric web 26 is aligned with and is of the same width as web 21 and also has an electrode 25 metallized on an upper face thereof. Electrodes 20 and 25 are of less width than that of webs 21 and 26 and extend from one longitudinal edge thereof leaving respective safe edges or bare margins 30, 34 of the web along opposite edges thereof. Electrode 20 extends from the left edge of web 21 and electrode 25 extends from the right edge of web 26.

In the exemplary embodiment of the present invention, electrodes 20 and 25 each have a thickness within the range of approximately 5–300 ohms/sq. It should be noted that a more preferred range is from approximately 50–250 ohms/sq. It should further be noted that the most preferred range is from approximately 120–230 ohms/sq.

Additionally, in the exemplary embodiment of the present invention, electrodes 20 and 25 are evenly matched in thickness within a specified tolerance. A preferred tolerance for the exemplary embodiment is ±2 ohms/sq. A more preferred tolerance is ±1 ohms/sq, and the most preferred tolerance is ±0.5 ohms/sq. For example, if electrode 20 is approximately 42 ohms/sq then, most preferably, electrode 25 is between approximately 41.5–42.5 ohms/sq.

In the exemplary embodiment of the present invention, electrodes 22 and 27 each have a thickness of approximately 1–2 ohms/sq. The thickness of electrodes 22 and 27 is greater than the thicknesses of electrodes 20 and 25 because they provide the base onto which the capacitor leads are attached by way of conventional spraying techniques. It is important to note that electrodes 22 and 27 should not extend into the active area 40 of the capacitor. The active area 40 is the portion of the capacitor between respective tolerance regions where a portion of electrode 20 overlaps a portion of electrode 25. If electrodes 22 and/or 27 extend into the active area 40, because they are constructed of relatively heavy metal (e.g., ~2 ohms/μ) rather than thin metal (e.g., ~40 ohms/μ), the improved dielectric strength achieved by reducing the thickness of electrodes 20 and 25 will be adversely affected.

There are several ways for providing the metallization in a metallized capacitor. One way is to use metal foil sheets, although, using current technology, producing foil sheets with the range of thicknesses employed by the present invention may be difficult.

Another way, and the preferred way in manufacturing capacitors employing the present invention, is vapor deposited metal. Vapor deposited metal techniques for standard metallization thickness use a boat for receiving the metal, typically, in wire form. The boat is heated so that a pool of metal is created which is continuously vaporized yet continuously replenished by incoming feed wire. The metal vapor is deposited on a material, typically, the dielectric which continuously passes through the vaporized metal. Standard metallization thicknesses (e.g., 1–4 ohms/sq) are achieved using a predetermined speed for feeding the metal wire into the boat as well as a separate predetermined speed for passing the dielectric through the vaporized metal.

One way to achieve the range of thicknesses for the present invention is to adjust the predetermined speeds for the metal wire feed and the passing dielectric. The speeds, which are independently adjustable, should be set to deposit the desired thickness of metallization on the dielectric. For example, this can be accomplished by increasing the speed of the wire feed, increasing the speed of the passing dielectric, or a combination of both.

It should be noted that most types of metals typically used for metallized film capacitors can be employed by the present invention. However, in the exemplary embodiment of the present invention, aluminum is preferred.

It should also be noted that most types of dielectrics typically used for metallized film capacitors can be employed by the present invention. In the exemplary embodiment of the present invention, polyester film is preferred while Mylar is most preferred. Mylar is a trademark of DuPont.

For an implantable defibrillator application, a metallized film capacitor can be produced to match or better the size of currently used electrolytic capacitors.

The metallized film capacitor uses a dielectric which is approximately 1.5μ thick with a manufacturer's cited dielectric strength of approximately 200 volts/μ. This means that according to the manufacturer, the dielectric breakdown voltage for the dielectric is approximately 300 volts (1.5μ times 200 volts/μ).

The capacitor in the defibrillator delivers approximately 30 joules per shot (or shock) to the patient. In order to generate 30 joules, the capacitor should charge to approximately 700 volts. Although, as described above, a capacitor in an implantable defibrillator may only be required to deliver 3–6 shots, the capacitor developed for this application can withstand approximately 200 shots for reliability purposes. Thus, for the capacitor to be capable of delivering 200 shots at 700 volts each, the dielectric breakdown voltage should be approximately 770 volts or 10% above the needed voltage (the 10% figure has been determined by way of experimental data).

With a required dielectric breakdown voltage of approximately 770 volts, the dielectric strength of the 1.5μ thick film should be increased from approximately 200 volts/μ to approximately 510 volts/μ. For this particular application, this is achieved by making the metallization thickness of each electrode between approximately 50–80 ohms/sq.

Figure 3A:
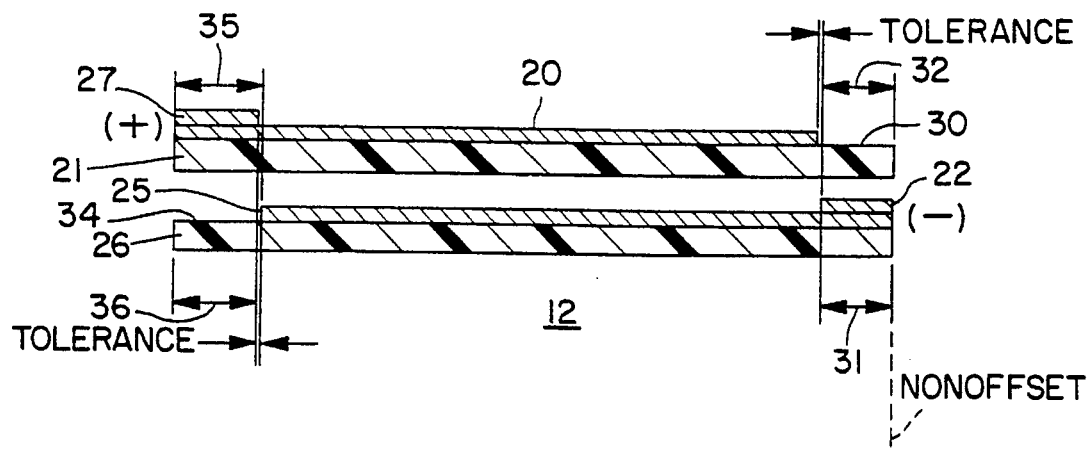
FIG. 3A shows a second exemplary embodiment of a metallized film capacitor employing the present invention.
Figure 3B:
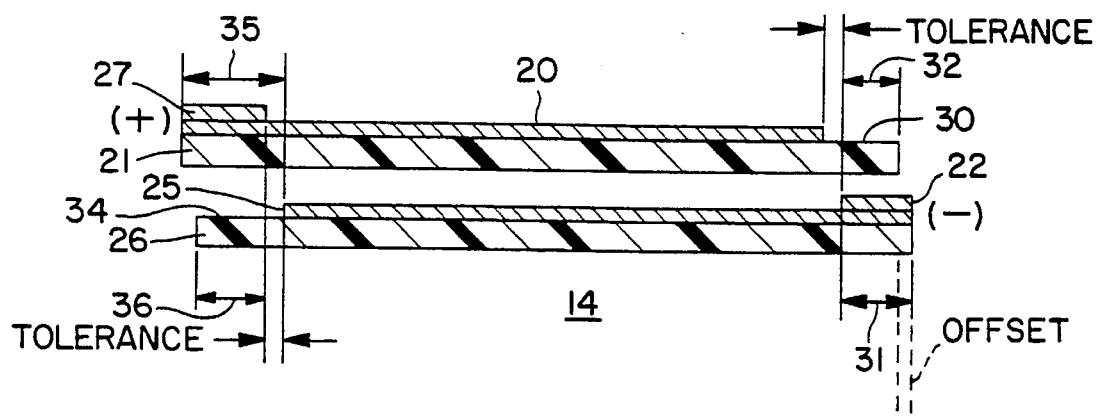
FIG. 3B shows the embodiment of FIG. 3A with an offset.

Referring now to the alternate embodiment of FIG. 3A, a non-offset capacitor 12 is shown comprising a first elongated dielectric web 21 having an electrode 20 metallized on an upper face thereof. A second elongated dielectric web 26 is aligned with and is of the same width as web 21 and also has an electrode 25 metallized on an upper face thereof. Electrodes 20 and 25 are of less width than that of webs 21 and 26 and extend from one longitudinal edge thereof leaving respective safe edges or bare margins 30, 34 of the web along opposite edges thereof. Electrode 20 extends from the left edge of web 21 and electrode 25 extends from the right edge of web 26.

In a preferred embodiment, electrodes 20, 25 are of equal width as are bare margins 30, 34. Margin 30 has a width 32 which together with the width of electrode 20 equals the total width of web 21. Similarly, margin 34 has a width 35 which together with the width of electrode 25 equals the total width of web 26.

As shown in FIG. 3A, the metallized webs 21 and 26 are disposed in superposed relation to each other with the bare margins 30, 34 respectively disposed at opposite edges of the superposed webs.

Electrodes 20 and 25 each include a second portion 27 and 22, respectively, which is relatively thicker than the remainder of the electrode. Second portions 27 and 22, for example, can be 1–4 Ohms/square; whereas, the remainder (or first portions) of electrodes 20 and 25, for example, can be 5–300 Ohms/square. The most suitable thickness for the first portions depends on the thickness (or guage) of the dielectric. For example, the following table illustrates some breakdown voltages achieved using a first portion thickness with a particular guage:

TABLE I

| DIELECTRIC THICKNESS (μ) | FIRST PORTION THICKNESS (Ohms/square) | BREAKDOWN VOLTAGE (Volts) |
|---|---|---|
| 1.58 | 200 | 800 |
| 1.60 | 150 | 780 |

Although Table I only presents two examples, as can be appreciated by those skilled in the art, various thicknesses can be employed for various guages in order to achieve a desired breakdown voltage.

Second portion 22, which is directly below margin 30, extends from the right longitudinal edge of web 21 which is opposite to that edge to which electrode 20 extends. Second portion 22 is of width 31 which is equal to width 32 less a manufacturing tolerance determined by the capabilities of the metallized film converters. Therefore, in the manufacturing process, even if second portion 22 extends to its maximum tolerance width, second portion 22 would not be formed under (opposing relationship with) electrode 20. It will be understood by those skilled in the art that in the manufacturing process that the tolerance may be exceeded in some few cases and second portion 22 may undesirably extend under electrode 20.

Similarly, second portion 27, which is directly above base margins 34, extends from the longitudinal edge (left edge) remote to that edge from which electrode 25 extends. Second portion 27 is of width 36 which is equal to width 35 of margin 34 less the manufacturing tolerance, so that substantially no portion of the area of second portion 27 extends below electrode 25.

It will now be understood that since second portions 22, 27 do not extend below their respective upper electrode layers 20, 25 that there is avoided the requirement for high voltage clearing between the respective upper and lower electrodes. In accordance with the invention as a result of having a greater surface exposed to the metal spray, there is a higher probability of excellent lead termination when the terminals are formed which produces minimum equivalent series resistance (ESR) and minimum dissipation factor. For example, on completion of the winding of the metallized webs into a capacitor roll, relatively thicker second portion provides a thicker surface area for the metal spray. Similarly, on rolling, second portion 27 provides a thicker surface area.

On completion of the winding of capacitor roll 10, the ends may be sprayed with a high velocity mixture of compressed air and molten fine particles of tin produced from an electric arc gun. This spray forms a first terminal (not shown) in contact with second portion 22 and a second terminal in contact with second portion 27. In conventional manner leads may then be respectively bonded to the terminals.

It will now be understood by those skilled in the art that during the winding process, even though webs 21, 26 are not offset prior to winding and even if there is travel of these webs as a result of machine inconsistencies or film distortion, there will always be on each end of the capacitor exposed metallization. For example, if web 21 wanders to the right with respect to web 26, then second portion 22 is exposed at the right end so that there is a connection between a sprayed terminal and second portion 22 which electrically connects to the rest of electrode 25. It is necessary that the dimension of width 31 be such that the maximum value of such travel is no greater than that dimension. It will further be understood that if the material wander, as shown in FIG.

3B, is such that web 26 wanders to the right with respect to web 21 then electrode 25 is exposed at the right end and is directly in contact with metal spray terminal. It should be noted that an exemplary offset is 0.01 inches.

The above description applies equally to the left end of capacitor 12 in which a wandering of web 26 to the left would expose electrode 27 and a wandering of web 21 to the left would expose electrode 20. Dimension 36 is also related to the maximum travel as above described. Thus, in accordance with the present invention, nonoffset wound capacitor 12 provides an increased volumetric efficiency while still permitting sufficient exposed metallization for proper termination even if the film is distorted or the material wanders during winding. It is in this way that the volumetric efficiency is increased by the amount of reduction in offset.

In view of the above, it will now be understood that in a further embodiment of the invention, width 31 of second portion 22 is less than width 32 of the safe edge less the tolerance. Specifically, width 31 of second portion 22 may be only sufficient to meet any irregularities due to the winding machine or film distortion. Thus, even though width 31 is narrower than width 32 (less the tolerance), and web 21 wanders to the right, for example, second portion 22 would still accept a spray terminal, thereby providing an effective capacitor connection. The foregoing also applies to width 36 of second portion 27 being less than margin width 35 (less the tolerance).

Figure 4:
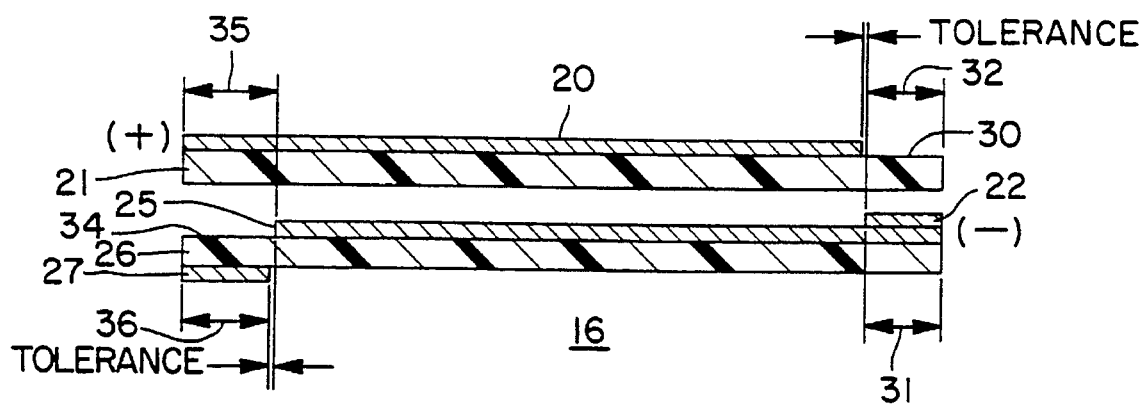
FIG. 4 shows a third exemplary embodiment of a metallized film capacitor employing the present invention.

Another exemplary embodiment is shown in FIG. 4. This embodiment is the same as that described and shown in FIG. 3A except only one of the electrodes (20 or 25) includes a second relatively-thicker portion and the other electrode (25 or 20) is formed in accordance with the techniques taught in U.S. Pat. No. 4,420,097. It should be noted that the side without the relatively-thicker second portion would desirably have a third electrode, as illustrated in FIG. 4, designated with reference numeral 29 and taught in the cited patent.

Figure 5:
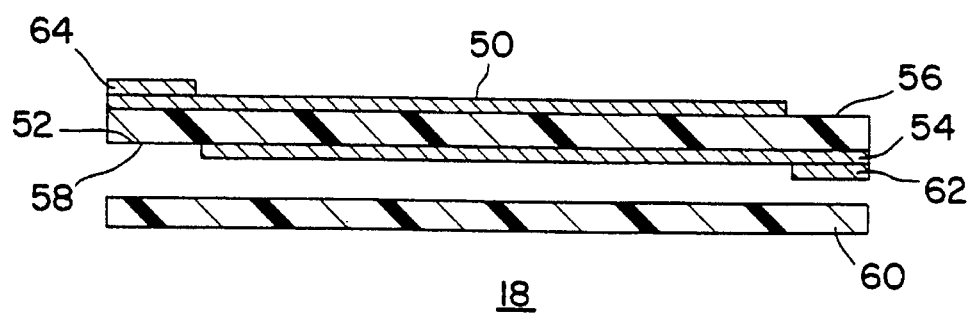
FIG. 5 shows a fourth exemplary embodiment of a metallized film capacitor employing the present invention.

Still another exemplary embodiment, shown in FIG. 5, includes a capacitor 18 which comprises a first elongated dielectric web 52 having an electrode 50 metallized on an upper face thereof. Electrode 50 extends from the left longitudinal edge of web 52 leaving a right safe edge or bare margin 56. A second electrode 54 is metallized on a lower face of web 52 and extends from the right longitudinal edge of web 52 leaving left safe edge or bare margin 58.

In accordance with this further embodiment of the invention, second web 60 is made substantially the same as and is aligned with first web 52. It should be noted that second web 60 is preferably 0.02 inches less than first web 52 in width.

Electrodes 50 and 54 each have relatively thicker second portions 64 and 62, respectively. Second portion 62, which is directly below margin 56, extends from the right longitudinal edge of web 60. Second portion 64, which is directly above margin 58, extends from the left longitudinal edge of web 60. Second portions 62, 64 are preferably about the same width as margins 56, 58 respectively.

Accordingly, in the winding of webs 60, 52, even though webs 52, 60 are of the same width, if there is travel between the webs during the winding process, there is always metallization at the respective end of the capacitor 10b. In this manner, a good electrical connection is provided with as low resistance as possible.

Figure 6:
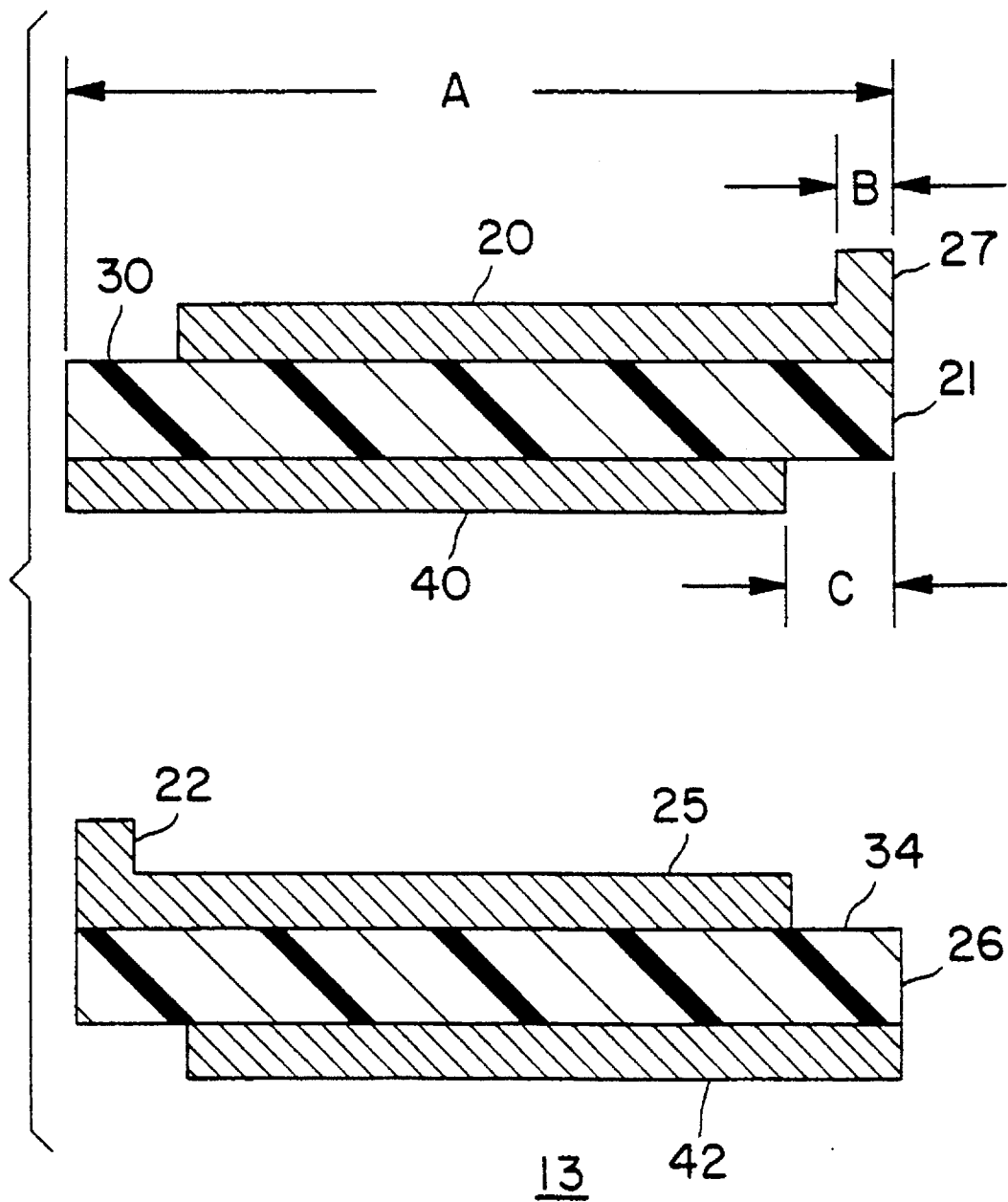
FIG. 6 shows a fifth exemplary embodiment of a metallized film capacitor employing the present invention.

FIG. 6 shows still another alternate embodiment for use with the present invention. This embodiment is similar to that shown in FIG. 3A except that metallization is used on both sides of the dielectrics 21 and 26. The use of the first and second additional layers of metallization 40 and 42 is a solution to a potential problem which can arise when using such thin metallization. The problem is the result of DC corona. If air or gas gets trapped between a layer of metallization (e.g., electrode 25) and the dielectric (e.g., dielectric 21) when winding, it can adversely affect the capacitor.

However, if metallization which extends into the active area is used on both sides of the dielectrics, as shown in FIG. 6, air trapped between two metallizations (e.g., 25 and 40) does not adversely affect the resulting capacitor.

Although the same thin metallization techniques are suitable for use with this embodiment, in the preferred embodiment of FIG. 6, metallization layers 20, 25, 40 and 42 are within the range of 120–230 ohms/square. Again, it is important that the opposing metallization layers are substantially the same thickness.

Also shown in FIG. 6 is the difference in width between width B and width C, thus providing space such that the heavy metal of portions 22 and 27 does not extend into the active region.

Although the invention is illustrated and described herein embodied as a capacitor having reduced metallization thicknesses for use in an implantable defibrillator, the invention is nevertheless not intended to be limited to the details as shown. Rather, various modifications may be made in the details within the scope and range of equivalents of the claims and without departing from the spirit of the invention.

What is claimed:

1. A metallized wound capacitor having increased dielectric breakdown, said capacitor having an active area, comprising:

first and second elongated dielectric webs each having a first face, a second face and a width;

a first electrode having first and second portions on the first face of the first web, the first electrode having a width less than the width of the first web;

a second electrode having first and second portions on the first face of the second web, the second electrode having a width less than the width of the second web;

the first and second electrodes extend from opposing dielectric web edges leaving respective bare margins along opposing edges on the respective webs, the second portion of the first electrode opposes the bare margin on the second web and the second portion of the second electrode opposes the bare margin on the first web, each second portion has a width equal to the opposing bare margin less a predetermined tolerance and is thicker than its respective first portion;

first and second additional metallization layers on the second face of respective webs, the first and second additional metallization layers extending into the active area from the opposite edge from which the first and second electrodes extend on the respective first faces, each of said first portions and said first and second additional metallization layers have thicknesses between 5–300 Ohms/square; and the dielectric webs being arranged in a capacitor roll with the first and second electrodes in superposed relation to each other.

2. The metallized wound capacitor of claim 1 in which said first portions of said first and second electrodes are substantially 200 ohms/square for a 1.58 micron dielectric web.

3. The metallized wound capacitor of claim 1 in which said first portions of said first and second electrodes are substantially 150 ohms/square for a 1.60 micron dielectric web.

4. The metallized wound capacitor of claim 1 in which said first portions and said first and second additional metallization layers are sufficiently thin in order to produce a breakdown voltage of greater than 700 volts.

5. The metallized wound capacitor of claim 1 in which the webs are offset one from the other prior to being convolutely arranged in a capacitor roll.

6. The metallized wound capacitor of claim 1 in which there are provided terminals formed by metal spray at the ends of the capacitor roll in contact with the respective first electrode of one web and the additional metallization of the other web.

7. The metallized wound capacitor of claim 1 in which said first portions of said first and second electrodes are greater than 14 Ohms/square.

8. The metallized wound capacitor of claim 1 in which said first portions and said first and second additional metallization layers are between 50–250 Ohms/square.

9. The metallized wound capacitor of claim 1 in which said first portions and said first and second aditional metallization layers are greater than 14 Ohms/square.

10. The metallized wound capacitor of claim 1 in which said first portions and said first and second additional metallization layers are between 40–70 Ohms/square.

11. The metallized wound capacitor of claim 1, wherein the first and second additional metallization layers have substantially the same thickness as the first portions of each of the first and second electrodes.

12. The metallized wound capacitor of claim 1 in which said second portions are between 1–4 Ohms/square.

13. A method of making a metallized wound capacitor having increased dielectric breakdown, said capacitor having an active area, comprising the steps of:

providing first and second elongated dielectric webs each having a first face, a second face and a width;

providing a first electrode having first and second portions on the first face of the first web, the first electrode having a width less than the width of the first web;

providing a second electrode having first and second portions on the first face of the second web, the second electrode having a width less than the width of the second web;

wherein the first and second electrodes extend from opposing dielectric web edges leaving respective bare margins along opposing edges on the respective webs, the second portion of the first electrode opposes the bare margin on the second web and the second portion of the second electrode opposes the bare margin on the first web, each second portion has a width equal to the opposing bare margin less a predetermined tolerance and is thicker than its respective first portion;

providing first and second additional metallization layers on the second face of respective webs, the first and second additional metallization layers extending into the active area from the opposite edge from which the first and second electrodes extend on the respective first faces, wherein each of said first portions and said first and second additional metallization layers have thicknesses between 5–300 Ohms/square; and arranging the dielectric webs in a capacitor roll with the first and second electrodes in superposed relation to each other.

14. The method of claim 13 in which said first portions of said first and second electrodes are greater than 14 Ohms/square.

15. The method of claim 13 in which said first portions and said first and second additional metallization layers are between 50–250 Ohms/square.

16. The method of claim 13 in which said first portions and said first and second aditional metallization layers are greater than 14 Ohms/square.

17. The method of claim 13 in which said first portions and said first and second additional metallization layers are between 40–70 Ohms/square.

18. The method of claim 13, wherein the first and second additional metallization layers have substantially the same thickness as the first portions of each of the first and second electrodes.

19. The method of claim 13 in which said second portions are between 1–4 Ohms/square.

* * * * *

UNITED STATES PATENT AND TRADE MARK OFFICE
CERTIFICATE OF CORRECTION

PATENT NO.    : 5,610,796
DATED         : March 11, 1997
INVENTOR(S)   : Lavene

It is certified that error appears in the above-identified patent and that said Letters Patent is hereby corrected as shown below:

Column 10, line 33, "aditional" should be --additional--.

Signed and Sealed this

Twenty-first Day of October 1997

Attest:

BRUCE LEHMAN

*Attesting Officer*       *Commissioner of Patents and Trademarks*